United States Patent [19]
Bley et al.

[11] Patent Number: 5,674,241
[45] Date of Patent: Oct. 7, 1997

[54] COVERED EXPANDING MESH STENT

[75] Inventors: Robert S. Bley, Menlo Park; Kevin H. Van Bladel, Mountain View; Joseph R. Thomas, San Carlos, all of Calif.

[73] Assignee: Menlo Care, Inc., Menlo Park, Calif.

[21] Appl. No.: 680,717

[22] Filed: Jul. 15, 1996

Related U.S. Application Data

[63] Continuation of Ser. No. 392,143, Feb. 22, 1995, abandoned.

[51] Int. Cl.$^6$ ........................................ A61M 29/00
[52] U.S. Cl. .............................. 606/198; 623/1; 623/12
[58] Field of Search .................... 606/1, 108, 192–195, 606/198, 200; 623/1, 11, 12

[56] References Cited

U.S. PATENT DOCUMENTS

| | | |
|---|---|---|
| 2,433,056 | 12/1947 | Masci . |
| 3,411,620 | 11/1968 | Steinbock . |
| 3,473,646 | 10/1969 | Burke . |
| 3,528,825 | 9/1970 | Doughty . |
| 3,570,485 | 3/1971 | Reilly . |
| 3,612,038 | 10/1971 | Halligan . |
| 3,677,243 | 7/1972 | Nerz . |
| 3,750,875 | 8/1973 | Juster . |
| 3,934,721 | 1/1976 | Juster et al. . |
| 4,033,382 | 7/1977 | Eichin . |
| 4,306,562 | 12/1981 | Osborne . |
| 4,411,655 | 10/1983 | Schreck . |
| 4,412,832 | 11/1983 | Kling et al. . |
| 4,424,305 | 1/1984 | Gould et al. . |
| 4,480,642 | 11/1984 | Stoy et al. . |
| 4,503,569 | 3/1985 | Dotter . |
| 4,512,338 | 4/1985 | Balko et al. . |
| 4,557,385 | 12/1985 | Robinson . |
| 4,610,357 | 9/1986 | Nakamura . |
| 4,648,867 | 3/1987 | Conner et al. . |
| 4,655,771 | 4/1987 | Wallsten . |
| 4,675,008 | 6/1987 | Tretbar . |
| 4,676,773 | 6/1987 | Sheldon . |
| 4,690,684 | 9/1987 | McGreevy et al. . |
| 4,699,611 | 10/1987 | Bowden . |
| 4,733,665 | 3/1988 | Palmaz . |
| 4,772,275 | 9/1988 | Erlich . |
| 4,779,727 | 10/1988 | Taterka et al. . |
| 4,798,867 | 1/1989 | Nakai et al. . |

(List continued on next page.)

FOREIGN PATENT DOCUMENTS

| | | |
|---|---|---|
| WO9005554 | 5/1990 | WIPO . |
| 9306781 | 4/1993 | WIPO . |
| 9424961 | 11/1994 | WIPO . |
| 9511055 | 4/1995 | WIPO . |

OTHER PUBLICATIONS

"About OB Tampons" International Article, Date Unknown.

"Development of Polymetic Shape Memory Material", Yoshiki Shirai & Shun–ichi Hayashi, Nagoya Research & Development Center, Technical Headquarters, MTE 184, Dec. 1988, pp. 1–5.

Johannes Lammer, MD, Fritz Flueckiger, MD, Klaus A. Hausegger, MD, Klaus A. Hausegger, MD, Guenther Erich Klein, MD, & Manuela Aschauer, MD, "Billary Expandable Metal Stents," Seminars in INterventional Radiology, vol. 8, No. 4, Dec. 1991, pp. 233–241.

Harold G. Coons, MD, "Self–Expanding Stainless Steel Biliary Stents," Radiology, Mar. 1989, vol. 170, No. 3 Part 2, pp. 979–983.

(List continued on next page.)

*Primary Examiner*—Guy V. Tucker
*Assistant Examiner*—William W. Lewis
*Attorney, Agent, or Firm*—Blakely, Sokoloff, Taylor & Zafman

[57] ABSTRACT

The present invention is a medical device such as a stent in the form of an expandable mesh with an expandable polymer layer thereon. The mesh is metal or plastic. The polymer may be any of a variety of expandable polymers, which either expand upon hydration, or expand without significant resistance. The invention may be used, for example, as an expandable biliary, vascular, endotracheal, esophageal, or prostatic device.

29 Claims, 4 Drawing Sheets

U.S. PATENT DOCUMENTS

| | | |
|---|---|---|
| 4,798,876 | 1/1989 | Gould et al. |
| 4,799,479 | 1/1989 | Spears |
| 4,811,847 | 3/1989 | Reif et al. |
| 4,877,132 | 10/1989 | Makris et al. |
| 4,878,903 | 11/1989 | Mueller |
| 4,878,906 | 11/1989 | Lindemann et al. |
| 4,883,699 | 11/1989 | Aniuk et al. |
| 4,911,691 | 3/1990 | Aniuk et al. |
| 4,922,905 | 5/1990 | Strecker |
| 4,923,061 | 5/1990 | Trombley, III |
| 4,925,448 | 5/1990 | Bazaral |
| 4,950,227 | 8/1990 | Savin et al. |
| 4,950,257 | 8/1990 | Hibbs et al. |
| 4,952,359 | 8/1990 | Wells |
| 4,994,047 | 2/1991 | Walker et al. |
| 5,026,377 | 6/1991 | Burton et al. |
| 5,041,085 | 8/1991 | Osborne et al. |
| 5,041,093 | 8/1991 | Chu |
| 5,041,126 | 8/1991 | Gianturco |
| 5,048,684 | 9/1991 | Scott |
| 5,061,275 | 10/1991 | Wallsten et al. |
| 5,067,612 | 11/1991 | Tsuchiya et al. |
| 5,071,407 | 12/1991 | Termin et al. |
| 5,078,720 | 1/1992 | Burton et al. |
| 5,089,005 | 2/1992 | Harada |
| 5,089,006 | 2/1992 | Stiles |
| 5,092,877 | 3/1992 | Pinchuk |
| 5,105,942 | 4/1992 | van Veen et al. |
| 5,123,917 | 6/1992 | Lee ................................. 623/1 |
| 5,131,537 | 7/1992 | Gonzales |
| 5,133,732 | 7/1992 | Wiktor |
| 5,139,480 | 8/1992 | Hickle et al. |
| 5,176,617 | 1/1993 | Fischell et al. |
| 5,178,611 | 1/1993 | Rosenberg |
| 5,221,263 | 6/1993 | Sinko et al. |
| 5,234,456 | 8/1993 | Silvestrini ........................ 623/1 |
| 5,234,457 | 8/1993 | Andersen |
| 5,282,789 | 2/1994 | Lundy |
| 5,282,823 | 2/1994 | Schwarz et al. .................. 623/1 |
| 5,332,092 | 7/1994 | Fischer |
| 5,383,928 | 1/1995 | Scott et al. ...................... 623/1 |
| 5,389,106 | 2/1995 | Tower ............................. 606/198 |
| 5,409,469 | 4/1995 | Schaerf |
| 5,445,646 | 8/1995 | Euteneuer et al. |

OTHER PUBLICATIONS

Plinio Rossi, MD, Mario Bezzi, MD, Filippo M. Salvatori, MD, Francesca Maccioni, MD & Mario L. Porcaro, MD, "Recurrent Benign Biliary Strictures: Management With Self–Expanding Metallic Stents," Radiology, vol. 175, No. 3, Jun. 1990, pp. 661–665.

Cook–Z Stents, Gianturco–Rosh Biliary Design, "Suggested Instructions for Placement," 3 pages.

IMPRA, The Fine Line of Excellence Brochure 6 pages.

Noriyuku Kato MD, Tadanori Hirano MD, Kan Takeda MD, Tsuyoshi Nakagawa MD, Tooru Mizumoto MD, Hiroshi Yuasa MD, Yasuhiko Shimizu MD, "Treatment of Aortic Dissections With a Percutaneous Intravascular Endoprosthesis: Comparison of Covered and Bare Stents," Journal of Vascular & Interventional Radiology, Nov.–Dec. 1994, pp. 805–812.

David M. Williams MD, James C. Andrews MD, Sam S. Chee BS, M. Victoria Marx MD, & Gerald D. Abrams, "Canine Model of Acute Aortic Rupture: Treatment with Percutaneous Delivery of a Covered Z Stent–Work in Progress," Journal of Vascular and Interventional Radiology, Nov.–Dec. 1994, pp. 797–803.

Thomas H. Barrows, "Synthetic Bioabsorbable Polymers," in High Performance Biomaterials. M. Szycher, ed. 1991, pp. 243–257.

Jamal Charara, Rovert Guidoin, Tian Jian Rao, Michel Marois, Juan Borzone, Yves Marois, Camille Gosselin & Nathan Sheiner, "Expanded PTFE Prostheses as Substitutes in the Abdominal Aorta of Dogs: A Comparative Study of Eleven Different Grafts," in High Performance Biomaterials. M. Szvcher. ed. 1991. pp. 287–311.

M–D–D–I Reports—"The Gray Sheet", Jan. 9, 1995 I&W–13–I&W–15.

Digestive Disease Week, May 10–13, 1992, p. 1828.

Joseph E. Oesterling, MD, "Urologic Applications of a Permanent, Epithelializing Urethal Endoprosthesis," Supplement to Urology, Jan. 1993, vol. 41, No. 1, pp. 10–18.

Eric C. Martin, MD, Karen J. Laffey, MD, PhD, Ronda Bixon, MD & George I. Getrajdman, MD, "Gianturco–Rosh Biliary Stents: Preliminary Experience," Journal of Vascular and Interventional Radiology, vol. 1 No. 1, Nov., 1990, pp. 101–105.

COOK–Z STENTS Gianturco–Rosh Biliary Design Brochure, Cook Incorporated, 4 pages.

"Ultraflex Esophageal Prosthesis: Setting New Standards For Management of Esophageal Obstruction", Microvasive Boston Scientific Corporation Brochure 6 pages.

COVERED EXPANDING MESH STENT

This is a continuation of application Ser. No. 08/392,143, filed Feb. 22, 1995, now abandoned.

BACKGROUND OF THE INVENTION

1. Field of the Invention

This invention relates generally to the field of stents for use primarily in ducts and vessels of the body, and more particularly, to the area of expandable stents which expand and/or reconform after implantation in the body.

2. Art Background

A number of biomedical devices have been used for the stenting of body passages that have become blocked or are otherwise damaged, or weakened. Expanding stents seem the most promising for this purpose because of the advantages provided by insertion of a small diameter tube-like device and the ultimate enlargement of the diameter to accommodate the flow of body fluids or food and the increase in time prior to occlusion of the stent.

There are a number of different types of devices for stenting of body passages that may be classified into two general categories: namely, expandable meshes which includes self-expanding types and non-self-expanding types, and non-expandable stents which are typically made of plastic or polymeric material. The self-expanding meshes can be made of a material, such as Nitinol, which changes configuration upon heating to body temperature. Other self-expanding meshes are made of resilient mesh material which can be flexed down into a small diameter tube and held in place in such a configuration until it is released, at which time it expands to a larger diameter configuration. The non-self-expanding meshes are expanded by use of an inflatable balloon which is placed inside the mesh in a small diameter configuration, and then inflated, thereby expanding the mesh to a larger diameter configuration. The balloon is then deflated for removal, leaving the mesh in its expanded configuration.

The expandable metal mesh stents are particularly advantageous in that they can increase in size up to 36 Fr. However, the metal meshes are difficult to remove since tissue in-growth occurs over time. A number of other problems, for example, mucosal hyperplasia, fungal proliferation, or neoplasm also are common with expandable metal mesh stents.

The expandable mesh stents can be made in a variety of materials such as, for example, stainless steel. The expandable mesh stents can be made in a variety of configurations such as a coiled spring, a variety of zig-zag patterns including various stents knows as "Z" stents, braided filament, and other collapsible configurations. One type of expandable stent comprises a cylindrical member having a slit cut along its length, so that the edges along the length can overlap to allow for compression to a reduced size. A further configuration which may be described as a perforated tube comprises a generally rigid tube with openings cut therein to allow for radial expansion under force of an expansion balloon or by expansion due to heating. The expandable mesh stents can be braided, woven, knitted, formed, molded, machined or made by other methods known in the art. Various mesh designs are disclosed, for example, in U.S. Pat. Nos. 4,512,338, 4,503,569, 4,922,905, 4,733,665, 4,950,227, 5,089,006 and 5,061,275. Other materials, configurations and methods of manufacture in addition to those described above are known.

As used herein, the term "expandable mesh" is meant to include, without limitation, self-expanding and non-self-expanding configurations made of any generally rigid or springy material which when expanded have an open network or arrangement which would otherwise allow tissue in-growth, and would not otherwise prevent fluid flow through its walls. Several of these prior art mesh stents have been utilized with a polymeric sheath or cover; however, since these sheaths must be stretched to increase in size, they exert a force that resists expansion, which tends to limit the final expanded size of the mesh. Additionally, this resistance may make expansion more problematic. Alternatively, the sheath may be folded or bundled over the mesh when it is compressed, so that no force is exerted upon expansion. However, this method increases the size of the compressed stent, so that a larger size catheter is required for a given size stent.

The plastic or polymeric stents exist only in smaller sizes because of the difficulty of inserting a larger catheter through the channel of existing scopes or in narrow body passages, such as veins or arteries, bile ducts, the esophagus, prostate, and the like. A disadvantage of the plastic stents is that as a result of the smaller size of the lumen, the plastic stents occlude faster than the expandable stents. One advantage of plastic or polymeric stents is that their closed structure prevents tissue in-growth which therefore makes it easier to remove, and less likely to be occluded by tissue in-growth from the outside. Some plastic or polymeric stents, as mentioned above, are simply small tubes.

With the current self-expandable mesh stents, the tubular body may comprise a flexible material where the diameter can be changed between a small diameter for insertion, and a final, expanded diameter after placement allowing for fluid flow therethrough. In some cases the self-expanding device assumes its final, expanded configuration when in an unrestricted condition, free of external forces in the radial direction. These type of devices must be compressed and loaded into a sheath that restrains the device radially for insertion into the body via a catheter. After insertion, the sheath or loading system may be removed to allow for expansion. After removal of the sheath, the device expands to its final diameter under spring-like forces resulting from the compression. In the case of heat sensitive materials, the stent takes on its expanded shape after it is heated above its transition temperature. With non-self-expanding mesh stents, upon expansion by the use of, for example, an expansion balloon, the final expanded configuration is achieved. Additionally, other methods of expansion and contraction are known.

What is needed is an expandable stent that allows for easy insertion and that increases in size to increase the time for occlusion to occur. The expandable stent should eliminate or minimize tissue in-growth without requiring a covering which either resists expansion or which must be folded or bundled when the stent is in the small radius, non-expanded condition. Further, it is desirable in some situations that the expandable stent does not require a loading sheath, so that a smaller sized catheter can be used to insert the stent into the body.

SUMMARY OF THE INVENTION

The present invention comprises an expandable mesh with an expandable polymer layer which can be on the inside of the expandable mesh stent, on the outside of the expandable mesh stent, within the interstices of the expandable mesh stent, or any combination of inside, outside and within the interstices of the mesh stent. The expandable polymer layer does not require either stretching or folding, nor does it exert a significant resistance to expansion.

The present invention may be used in a number of different fields of medicine: products may include expandable biliary, vascular, endotracheal, esophageal, and prostatic devices. The size and design may be different for each medical application.

In one embodiment of the present invention, the polymer layer is expandable by hydration. For example, the polymer layer may comprise a member of the family of polymers sold under the trademarked name AQUAVENE®, examples of which are described in U.S. Pat. Nos. 4,883,699 and 4,911,691. Other expandable polymers which expand by hydration known in the art include HYPAN® (Hydrolyzed polyacrylonitrile) (U.S. Pat. No. 4,480,642), hydrophilic polyether polyurethane (U.S. Pat. No. 4,798,876), polyurethane diacrylate (U.S. Pat. No. 4,424,305), and various hydrogels, including cross-linked PVP (polyvinyl pyrrolidone), PVA (polyvinyl alcohol), PEO (polyethylene oxide) and pHEMA (poly (hydroxyethyl methacrylate)).

The hydrophilic polymer AQUAVENE® comprises a combination of a non-hydrophilic component (e.g., an elastomer such as urethane, silicone, PVC or the like) and a hydrophilic component (a hydrogel) which allows the material to swell and increase in size and maintain strength as outlined, for example, in U.S. Pat. No. 4,883,699. In a preferred embodiment the amount of expansion of the polymer layer is approximately equivalent to the amount of expansion of the mesh in the expanded condition. The amount of expansion of a material or device may be described by the expansion ratio. For the mesh, this may be the ratio of, for example, the diameter in the compressed condition to the diameter in the unrestricted, expanded condition. For the polymer layer, the expansion ratio may be the ratio of the diameter in the non-hydrated state to the diameter in the fully hydrated state. In the case of AQUAVENE®, the ratio of hydrophilic to non-hydrophilic component controls the amount of expansion of the material upon hydration, so that the amount of polymer expansion can be matched with the amount of expansion of the mesh. Under a currently preferred embodiment of the present invention, the elastomer content should generally be in the range of approximately 15–75%, and preferably 20–65%, and more preferably 25–30% by volume in the dry (non-hydrated) state.

In an alternative embodiment of the present invention, the polymer layer comprises a material which, by virtue of its method of manufacture, or, e.g., arrangement of the knit, may expand between a first, smaller configuration and a second, larger configuration without requiring stretching of the material to the larger configuration, so that the polymer layer can be expanded without offering significant resistance. Further, the material does not require folding or bunching to be placed in the smaller configuration, so that the presence of the material does not significantly increase the size of the compressed stent or reduce the size of the lumen.

One advantage of the present invention is the elimination of the open mesh of the prior art. The closed smooth surface of the polymer layer prevents tissue and tumor in-growth and allows for easier removal of the prosthesis. It is recognized that there has been some use in the field of expandable meshes combined with polymeric materials which must stretch to expand as described earlier. However, in accordance with one embodiment of the present invention, the polymeric materials also self-expand, and can be devised to expand approximately the same degree as the open mesh. In accordance with a further embodiment, the polymer layer can change from a small configuration to a larger configuration without significant resistance. Thus, unlike prior art devices which either do not have any polymer layer, or which have a polymer layer which stretches with some resistance, the present invention allows for expansion of the mesh with no substantial resistance. It will be recognized however, that even if there is a small amount of resistance by the polymer layer, it may be within the spirit and scope of the present invention.

An advantage of the present invention relative to the use of the above described self-expandable polymers alone is that the expandable mesh provides a resistance to crushing which is much greater than the resistance to crushing of the polymer alone if the polymer formulation were such that it would expand as much as the mesh. The structure of polymeric stents of self-expandable polymer which resist crushing may require excessively thick walls, which would either defeat the purpose of attempting to make the outside diameter as small as possible for easy insertion, or alternatively, make the internal diameter very small thereby defeating the purpose of using the stent to allow a larger volume of fluid to pass through the duct. The expandable mesh of the present invention provides the mechanical strength necessary to prevent occlusion due to lateral forces such as from tumor growth.

Another advantage of the present invention is the ability to load additives into the hydrophilic polymer which may be released at a controlled rate. The additives may include, for example, antibacterial, anti-microbial, anti-calcification, growth hormones, anti-cancer-related drugs, anti-thrombogenic agents, and anti-restenosis agents which are beneficial in conjunction with, or in addition to the implantation of the stent.

In addition, the present invention still has the advantage of the expandable meshes which allow for the implantation of smaller prosthesis which thereafter increase in lumen size after insertion for greater flow rate, and longer implantation time prior to occlusion.

The design of the expandable mesh may consist of any type of self-expanding meshes such as those described in the above-mentioned patents. The mesh may be a self-expandable mesh capable of collapsing to a smaller diameter and expanding if it is not held radially by a sheath, or in the case of heat-sensitive materials, until the temperature rises above the transition temperature of the material. In some embodiments, the expandable mesh may also be of the non-self expanding type which requires a separate force, typically an expansion balloon, to cause the expansion.

In an embodiment of the invention, the expandable hydrophilic polymer layer holds the expanding mesh until the hydrophilic component of the polymer layer hydrates inside the body. The polymer layer after hydration softens, swells, and expands to allow the contracted mesh to expand. In alternative embodiments, some expandable configurations of non-hydrophilic polymer layers have a structure such that they can change between a small to a large configuration without significant resistance and without folding or bunching in the small configuration. Under such circumstances, these polymer layers can be expanded along with the expandable mesh, either under the force of expansion from the mesh and/or under pressure from an expansion balloon.

DETAILED DESCRIPTION OF THE INVENTION

The present invention comprises a stent or other medical generally tube-like device for implantation in the body on a temporary, semi-permanent or permanent basis, the invention comprising an expandable mesh with an expandable polymer layer on the inside of the mesh stent, on the outside of the mesh stent, within the interstices of the mesh stent or any combination thereof.

Figure 1:
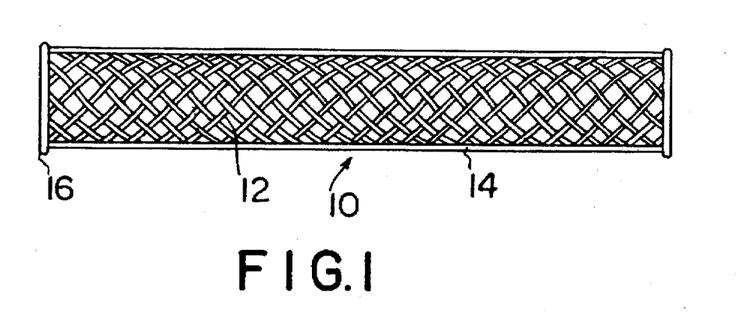
FIG. 1 is a sectional view of an embodiment of the present invention in collapsed condition.

As shown in FIG. 1, an embodiment of the present invention comprises a tubular shaped stent 10 comprising a mesh 12 and an outer polymer layer 14. In the embodiment shown in FIG. 1, the outer polymer layer 14 covers all or most of the outer surface of mesh 12. However, the outer polymer layer 14 is shown only at the top and bottom edges of the Figure for purposes of illustration to allow viewing of mesh 12. In general, outer polymer layer 14 is a sheath-like structure which may be attached to the mesh 12 in a variety of ways as discussed later. A retention flange 16, or other mechanism, such as exposed wires, may be provided, to assist in maintaining the positioning of the structure after placement in the body, as is known in the prior art. FIG. 1 shows the stent in a collapsed position which is useful for initial insertion of the stent into the body.

Figure 2:
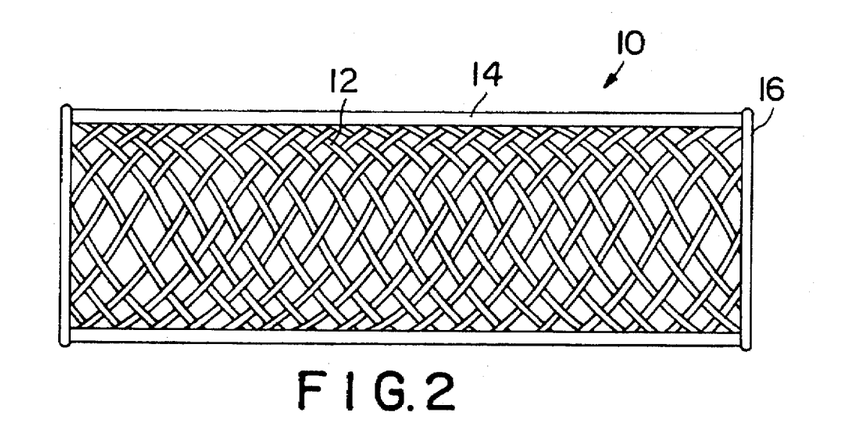
FIG. 2 is a sectional view of the embodiment of the present invention of FIG. 1 in an expanded condition.

Referring to FIG. 2, the present invention 10 is now shown in its expanded condition. It still comprises mesh 12 and an outer polymer layer 14, again shown only at the top and bottom edges of FIG. 2 for purposes of illustration. In the condition shown in FIG. 2, the stent 10 may have been inserted into a duct in the body from which outer polymer layer 14 has absorbed water and expanded. The outer polymer layer 14 upon expansion, no longer holds mesh 12 in the collapsed position, so that it too expands to the configuration shown in FIG. 2.

Figure 3:
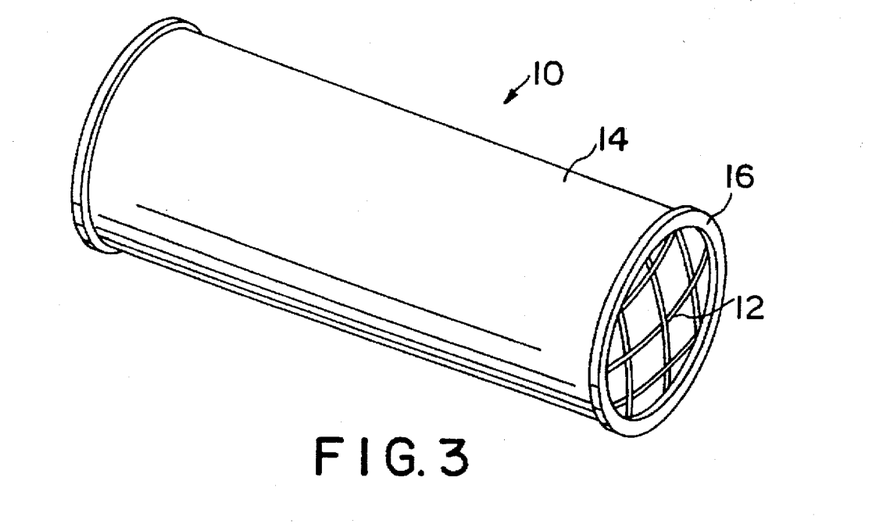
FIG. 3 is a perspective view of the embodiment of the present invention of FIG. 1 and 2.

FIG. 3 shows expanded stent 10 in perspective view. As can be seen, the mesh 12 is substantially completely covered by outer polymer layer 14.

Figures 4, 5:
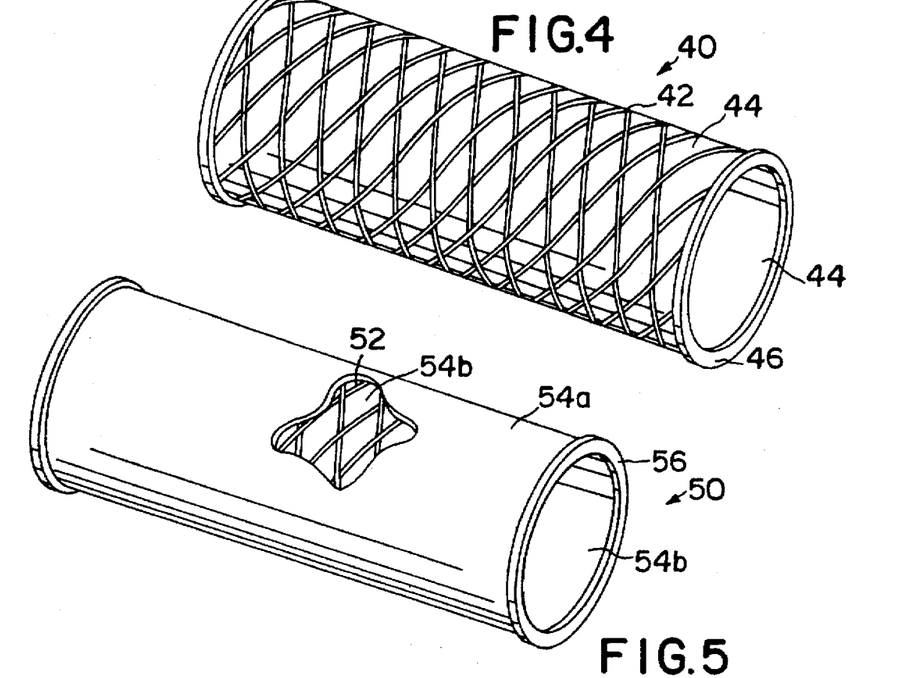
FIG. 4 is a perspective view of a further embodiment of the present invention.
FIG. 5 is a perspective view of a further embodiment of the present invention.

FIG. 4 shows an alternative embodiment of the present invention. As shown, stent 40 comprises mesh 42 and inner polymer layer 44. Inner polymer layer 44 is similar to outer polymer layer 14 of FIGS. 1-3, with the exception that it is disposed within the mesh 42. Again, the stent 40 may have retention flange 46, or similar mechanism.

FIG. 5 shows a further alternative embodiment of the present invention. In FIG. 5, stent 50 comprises mesh 52, outer polymer layer 54a and inner polymer layer 54b. A portion of outer polymer layer 54a is cut-away for purposes of illustration for viewing of mesh 52, and inner polymer layer 54b within mesh 52. The outer and inner polymer layers 54a and 54b are similar to polymer layer 44 of FIG. 4, and outer polymer layer 14 of FIGS. 1-3.

Figure 6:
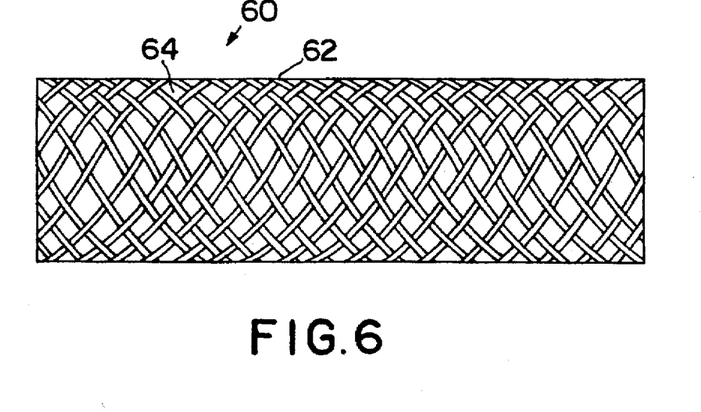
FIG. 6 is a view of a sectional view of a further embodiment of the present invention.
Figure 7:
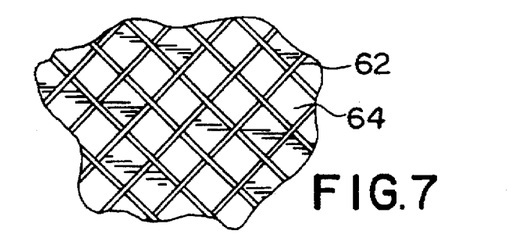
FIG. 7 is a view of a portion of the embodiment of FIG. 6.

FIG. 6 shows a sectional view of stent 60. In this embodiment, stent 60 comprises a mesh 62 with polymer layer 64 disposed within the interstices of mesh 62. Although not shown, stent 60 may have a retention flange or other means to hold the stent in place within the body. The polymer layer 64 is similar to the layers 54, 44 and 14 of the previous embodiments, with the exception, instead of being sheath-like as in layers 14 and 54a, or liner-like as in layers 44 and 54b, the polymer layer 64 is now disposed within the interstices of mesh 62. Typically, an interstitial polymer layer is formed in conjunction with an inner layer, an outer layer, or both. FIG. 7 shows a portion of the stent 60 of FIG. 6.

A number of materials may be used for the expandable mesh, such as stainless steel, tantalum, gold, titanium, nitinol heat sensitive material, or any suitable plastic material that may be formed so it may be collapsed, and when released, expand radially. The expandable mesh may be self-expanding. Alternatively, the mesh may not be self-expanding, which would require external, or more typically, internal assistance, usually in the form of an expansion balloon. The mesh may be any configuration and may be made in any manner, such as is disclosed in the earlier cited patents.

Figure 8:
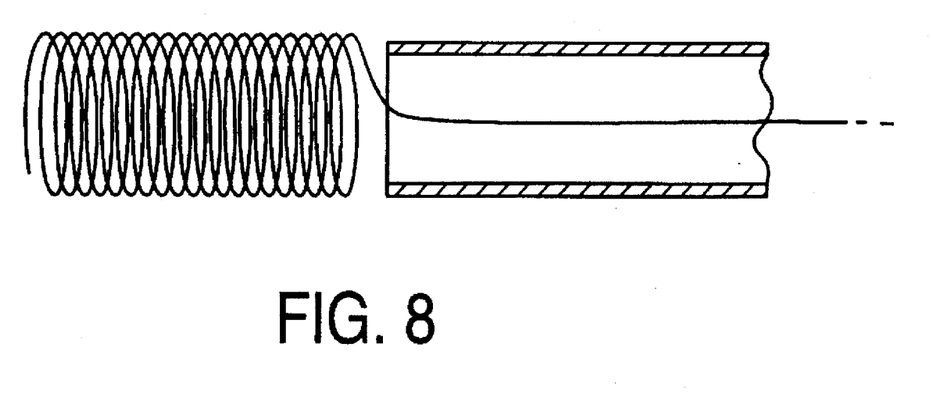
FIG. 8 shows an example of a coiled spring configuration.
Figure 9:
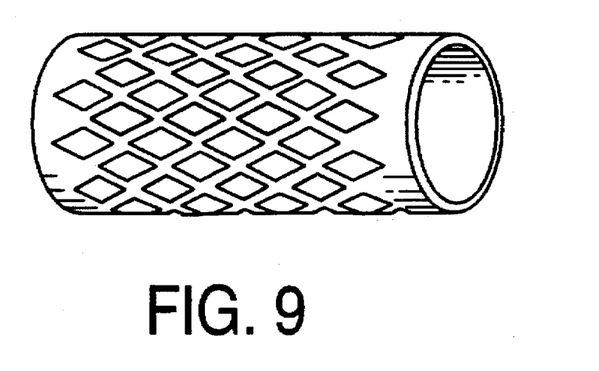
FIG. 9 shows an example of a perforated tube configuration.
Figure 10:
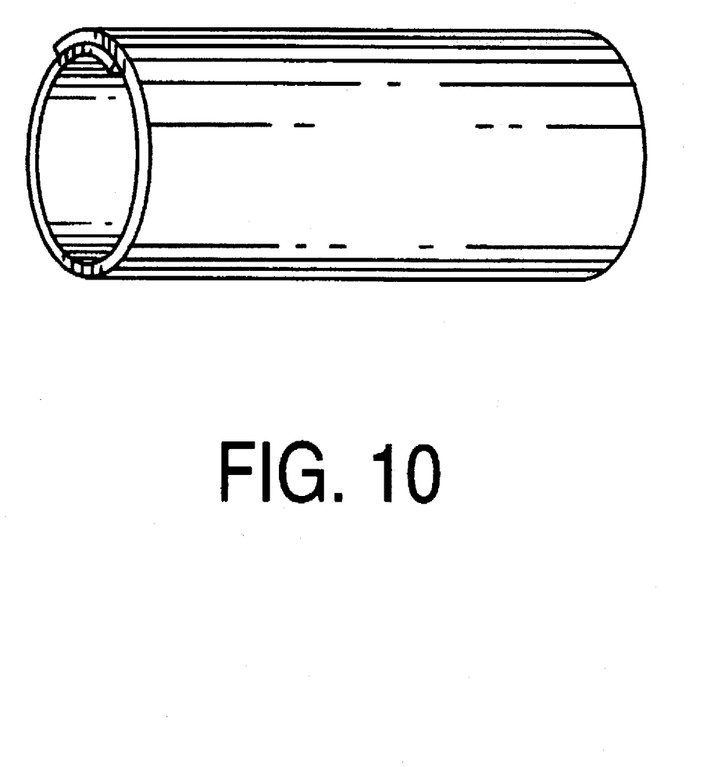
FIG. 10 shows an example of a slit tube configuration.
Figure 11:
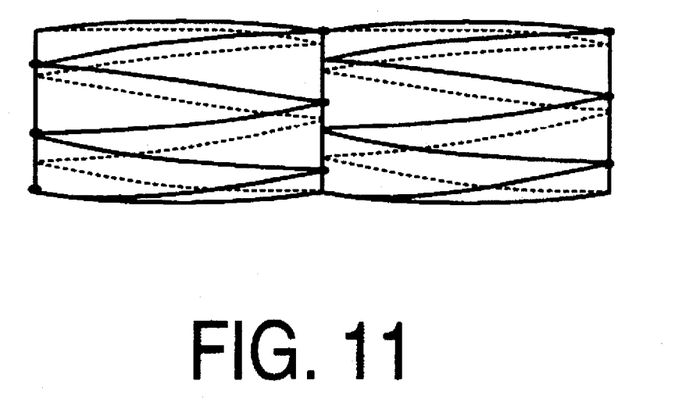
FIG. 11 shows an example of a zig-zag configuration.

For example, the mesh may be a braided filament as shown in FIGS. 1 through 7 herein. Alternatively, other configurations may be used, such as a coiled spring, an example of which is shown in FIG. 8, a perforated tube, as shown in FIG. 9, a slit tube, an example of which is as shown in FIG. 10, or a zig-zag configuration as shown in FIG. 11.

The polymer layers, such as layers 14, 44, 54a, 54b and 64 of the present invention may be one of the earlier described hydrophilic polymers, which expand upon hydration. Alternatively, these polymer layers may be made of a material which expands from a first, smaller configuration to a second, larger configuration, without requiring stretching and without exerting significant force against expansion. Further, the material does not require folding or bunching to contract from the expanded, larger configuration to the smaller configuration. One material which has this property is expanded polytetrafluoroethylene (PTFE). Typically, expanded PTFE is fabricated by pulling or expanding the PTFE after extrusion so that the PTFE is expanded in a longitudinal direction. The expanded PTFE has the above-described property of being capable of being "pushed" and "pulled" between a shorter and longer length, without requiring stretching, or exerting significant resistance against expansion when going from the shorter to the longer length, and without requiring folding or bunching of the PTFE when being pushed into the shorter length from the longer length.

In the present invention, since it is desirable for the polymer layer to expand radially after insertion into the body, the PTFE may be radially expanded after extrusion. The radially expanded PTFE may be used, for example, as the polymer layer 14 of FIGS. 1 and 2. The PTFE layer 14 may be placed on the mesh 12 in the configuration shown in FIG. 1, without requiring folding or bunching of the material 14, and then expand to the configuration shown in FIG. 2, without offering significant resistance, and without limiting the final expanded diameter. As an alternative to radially expanded PTFE, longitudinally expanded PTFE may be used provided it is disposed on the mesh 12 such that its direction of expansion is radial. For example, a length of longitudinally expanded PTFE may be cut and wrapped around an expandable mesh 12 with the longitudinal direction perpendicular to the length of the mesh. The expanded PTFE may be desirable in comparison to a hydrophilic polymer layer when mesh 12 is non-self-expanding, since the mesh 12 can be expanded by an expansion balloon, without any significant resistance from the polymer layer during expansion. In contrast, in using a non-self-expanding mesh in combination with a hydrophilic polymer layer, it would be necessary to wait until hydration of the hydrophilic polymer prior to expansion.

In addition to expanded PTFE described above, other polymers, such as, for example, dacron may be used in the present invention. If the polymer is not expanded as with PTFE, the structure of the material should be such that the material has the above-described ability to assume a small, compressed configuration and a larger expanded configuration, without requiring stretching to the larger configuration, and without requiring folding to the smaller configuration. The material may have this property by virtue of a weave or structure in which the fibers or filaments of the material are not aligned substantially longitudinally in the direction of expansion. In this way the material has some range of movement where the fibers or filaments of the material move in an accordion or bellows-like fashion. While, on a small scale the fibers or filaments of the material may fold in on themselves upon compression, it should be noted that no large scale folding or bunching of the material occurs, so that the compression to the small size does not significantly increase the required size of the catheter. With regard to this embodiment of the invention, the expansion ratio of the material may be described as, for example, the ratio of the expanded diameter to the compressed diameter, where the compressed diameter is the diameter at which the material is compressed to its smallest size without requiring folding or bunching on a large scale, and the expanded diameter is the diameter when the material has been expanded as far as possible without stretching. It will be appreciated that a material such as expanded PTFE, or other materials as described herein, may expand beyond this, but stretching would be required.

A preferred material to use for holding the mesh in a collapsed position, until insertion in the body where it allows the mesh to expand, is a hydrophilic polymer such as that sold under the tradename AQUAVENE®. An AQUAVENE® polymer is a co-continuous blend of a non-hydrophilic polymer (elastomer) and a hydrophilic polymer (hydrogel). In a preferred embodiment, the hydrophilic component is generally in the range of approximately 15–75%, preferably 20–65% and more preferably 25–30%, by volume in the dry (non-hydrated) state. Some amount of the non-hydrophilic component is desirable to provide some physical integrity of the polymer sufficient for the purposes of the present invention. However, a cross-linked hydrogel alone can be used. It should be noted that although, as described earlier, the mesh provides a greater crush resistance than a hydrophilic polymer of the same expansion ratio, the hydrophilic polymer provides some crush resistance, so that the present invention provides enhanced crush resistance as compared with either the mesh alone or the polymer alone.

The stent of the present invention may be formed by a number of different techniques in a number of different configurations. For example, a hydrophilic polymer layer, in the form of a sheath, may be bonded to the expandable mesh in its collapsed position so that the "dry" polymer holds the expandable mesh in a collapsed state. Alternatively, the polymer layer may be laminated, imbedded, coated, extruded, incorporated, or molded around the expandable mesh in its collapsed condition. Upon hydration inside the body, the polymer layer expands and looses its ability to restrain the expandable mesh, allowing the mesh to expand radially. In some cases, it may be necessary to allow the polymer layer to move relative to the expandable mesh. For example, it may be desirable to use a polymer layer in the form of a sheath placed external and/or internal to the expandable mesh which is not bonded to or embedded within the mesh, so that the polymer layer does not bind the filaments of the mesh, thereby preventing it from fully expanding. In many cases, however, the polymer layer may be so bonded or embedded, as the polymer layer in the hydrated state allows for sufficient movement of the filaments of the mesh to allow it to self expand. The polymer layer of an embodiment using expanded PTFE or similar material may be coupled to the mesh using the above techniques. However, this type of polymer layer by itself will not hold the mesh in the collapsed configuration.

In the present invention, the expandable polymer layer or layers are designed such that they have an approximately equal expansion ratio as the expandable mesh. In this way, the expandable polymer layer does not in any way resist the expansion of the expandable mesh, allowing for full expansion of the mesh. It will be appreciated that there may be a slight mismatch in expansion ratios without significantly affecting the performance of the device. Further, if desired, the expansion ratio of the hydrophilic polymer layer may be provided such that it assists in the expansion of the mesh. For example, the hydrophilic polymer layer may have a slightly greater expansion ratio, which may enable some meshes to expand to a slightly larger size than the mesh would expand without the presence of the hydrophilic polymer layer.

As described above, the polymer layer may be placed externally, internally within the interstices of the mesh, or any combination thereof. Typically, the placement of a polymer layer interstitially may be achieved in conjunction with an external or internal layer. One preferred embodiment is to form the polymer layer both internal and external to the mesh in its collapsed position, so that the stent has a smooth inner lumen and a smooth outer surface. The smooth outer surface allows for easier removal of the stent, while a smooth inner surface may be helpful in increasing the time until occlusion occurs. In embodiments using a hydrophilic polymer layer, the polymer layer may expand through the mesh to some extent, so that a single polymer layer either internal or external, may provide a smooth surface both internal and external of the mesh. Further, an advantage of embodiments using a hydrophilic polymer layer which forms a hydrogel is that the hydrogel is typically highly biocompatible.

The existing self-expanding meshes must be pre-loaded in a sheath delivery system, which holds the mesh in a tight configuration. The present invention may eliminate the need for a sheath in some cases, since the hydrophilic polymer layer of the present invention restricts the mesh in a collapsed position until after insertion and until the polymer layer is sufficiently hydrated. This arrangement can allow for a smaller external diameter delivery system than if a sheath is necessary, because the additional diameter of the sheath becomes unnecessary since its function is undertaken by the polymer layer. In some cases, if the polymer layer hydrates too quickly a sheath may be necessary to allow placement of the stent prior to hydration. Alternatively, if desired, a coating could be applied to the polymer layer to slow down the hydration. The coating may be similar to a material used to make time release drugs, or absorbable sutures. The coating may be designed to take any desired predetermined amount of time to dissolve, to allow for any desired amount of time in which to place and maneuver the stent in the body. For examples of the suitable materials, see, for example, Barrows, Thomas H., "Synthetic Bioabsorbable Polymers," in *High Performance Biomaterials*. M. Szycher, ed. 1991, pp. 243–257.

As described above, the polymer layer may comprise a hydrophilic polymer, or may comprise an expandable polymer that expands without stretching, such as expanded PTFE. Additionally, the polymer layer may be internal, and/or external, and/or interstitial. It will be appreciated that in an embodiment having more than a single layer, one or more of the layers may comprise a hydrophilic polymer and one or more of the layers may comprise a material such as expanded PTFE, if desired. Such an embodiment may be useful for delaying hydration for some period, so that the stent may be placed. For example, one or more hydrophilic polymer layers may be disposed internal, and/or external, and/or interstitial of the mesh stent. An expanded PTFE layer, for example, may then be placed internal and/or external to any hydrophilic polymer layers to delay hydration.

The above present invention may be used in a number of different fields of medicine: products may include expandable biliary, vascular, endotracheal, esophageal, and prostatic devices. The size and design may be different for each medical application.

It will be obvious to a person of ordinary skill in the art that numerous modifications and changes can be made to the above apparatus in order to accomplish the same function without departing from the spirit and scope of the present invention.

What is claimed is:

1. A stent for insertion into the interior of a body comprising:
   an expandable stent body, said expandable stent body having a first configuration having a first diameter and a second configuration having a second diameter wherein said first diameter is less than said second diameter; and,
   an expandable polymer layer coupled with said expandable stent body, said expandable polymer layer being hydrophilic, said expandable polymer layer expanding upon hydration to form an expanded polymer layer, said expanded polymer layer coupled with said expandable stent body as one of an internal liner-like layer inside said expandable stent body an external sheath-like layer outside said expandable stent body, an interstitial layer disposed within interstices in said expandable stent body, and any combination thereof.

2. The stent of claim 1 wherein said expandable stent body is self-expanding.

3. The stent of claim 2 wherein said expandable polymer layer holds said expandable stent body in said first configuration prior to hydration of said expandable polymer layer, and allows said expandable stent body to expand to said second configuration upon hydration of said expandable polymer layer.

4. The stent of claim 1 wherein said expandable stent body comprises a material selected from the group consisting of stainless steel, tantalum, gold, titanium, nitinol, and plastic.

5. The stent of claim 1 wherein said expandable stent body has a configuration selected from the group consisting of coiled spring, braided filament, perforated tube, slit tube, and zig-zag.

6. The stent of claim 1 wherein said expandable polymer layer comprises a material selected from the group consisting of: a blend of a hydrophilic polymer and a non-hydrophilic polymer, hydrolyzed polyacrylonitrile, hydrophilic polyether polyurethane, polyurethane diacrylate, polyvinyl pyrrolidone, polyvinyl alcohol, polyethylene oxide and poly (hydroxyethyl methacrylate).

7. The stent of claim 1 said expandable polymer layer has an additive contained therein.

8. The stent of claim 7 wherein said additive is selected from the group consisting of antibacterial, anti-microbial, anti-calcification, anti-encrustation, growth hormones, anti-cancer-related drugs, medicaments, anti-thrombogenic agents, and anti-restenosis agents.

9. The stent of claim 1 wherein said expandable stent body has a first expansion ratio and said expandable polymer layer has a second expansion ratio, wherein said first and said second expansion ratio are approximately equal.

10. The stent of claim 1 wherein said stent has an enhanced expansion force compared with said expandable stent body alone and said expandable polymer layer alone.

11. The stent of claim 1 wherein said stent has an enhanced crush resistance compared with said expandable stent body alone and said expandable polymer layer alone.

12. The stent of claim 1 wherein said expandable polymer layer inhibits tissue in-growth through walls of said stent.

13. The stent of claim 1 wherein said expandable polymer layer inhibits liquid flow through walls of said stent.

14. A stent for insertion into the interior of a body comprising:
   an expandable stent body, said expandable stent body having a first configuration having a first diameter and a second configuration having a second diameter wherein said first diameter is less than said second diameter; and,
   an expandable polymer layer coupled with said expandable stent body, said expandable polymer layer being hydrophilic, said expandable polymer layer expanding upon hydration, wherein said expandable polymer layer has a coating thereon, said coating delaying hydration of said expandable polymer layer for a predetermined time.

15. A stent for insertion into the interior of a body comprising:
   an expandable stent body, said expandable stent body having a first configuration having a first diameter and a second configuration having a second diameter wherein said first diameter is less than said second diameter, said expandable stent body having a tendency to expand from said first configuration to said second configuration; and,
   an expandable polymer layer coupled with said expandable stent body, said expandable polymer layer being hydrophilic, said expandable polymer layer expanding upon hydration to form an expanded polymer layer, said expandable polymer layer holding said expandable stent body in said first configuration prior to expansion, said expandable polymer layer remaining coupled to said expandable stent body after expansion.

16. The stent of claim 15 wherein said expandable stent body is self-expanding.

17. The stent of claim 16 wherein said expandable polymer layer holds said expandable stent body in said first configuration prior to hydration of said expandable polymer layer, and allows said expandable stent body to expand to said second configuration upon hydration of said expandable polymer.

18. The stent of claim 15 wherein said expandable stent body comprises a material selected from the group consisting of stainless steel, tantalum, gold, titanium, nitinol, and plastic.

19. The stent of claim 15 wherein said expandable stent body has a configuration selected from the group consisting of coiled spring, braided filament, perforated tube, slit tube, and zig-zag.

20. The stent of claim 15 wherein said expandable polymer layer comprises a material selected from the group consisting of: a blend of a hydrophilic polymer and a non-hydrophilic polymer, hydrolyzed polyacrylonitrile, hydrophilic polyether polyurethane, polyurethane diacrylate, polyvinyl pyrrolidone, polyvinyl alcohol, polyethylene oxide and poly (hydroxyethyl methacrylate).

21. The stent of claim 15 wherein said expandable polymer layer is disposed on one of the inside of said expandable stent body, the outside of said expandable stent body, the interstices of said expandable stent body, and any combination thereof.

22. The stent of claim 21 wherein said expandable stent body has a first expansion ratio and said expandable polymer layer has a second expansion ratio, wherein said first and said second expansion ratio are approximately equal.

23. The stent of claim 15 said expandable polymer layer has an additive contained therein.

24. The stent of claim 23 wherein said additive is selected from the group consisting of antibacterial, anti-microbial, anti-calcification, anti-encrustation, growth hormones, anti-cancer-related drugs, medicaments, anti-thrombogenic agents, and anti-restenosis agents.

25. The stent of claim 15 wherein said expandable polymer layer has a coating thereon, said coating delaying hydration of said expandable polymer layer for a predetermined time.

26. The stent of claim 15 wherein said stent has an enhanced expansion force compared with said expandable stent body alone and said expandable polymer layer alone.

27. The stent of claim 15 wherein said stent has an enhanced crush resistance compared with said expandable stent body alone and said expandable polymer layer alone.

28. The stent of claim 15 wherein said expandable polymer layer inhibits tissue in-growth through walls of said stent.

29. The stent of claim 15 wherein said expandable polymer layer inhibits liquid flow through walls of said stent.

\* \* \* \* \*